US00PP33692P2

(12) United States Plant Patent
Holtmaat

(10) Patent No.: US PP33,692 P2
(45) Date of Patent: Nov. 23, 2021

(54) ***ECHINACEA* PLANT NAMED 'PIN449'**

(50) Latin Name: ***Echinacea* hybrid**
Varietal Denomination: PIN449

(71) Applicant: Henricus Maria Joseph Holtmaat, Zuidwolde (NL)

(72) Inventor: Henricus Maria Joseph Holtmaat, Zuidwolde (NL)

(73) Assignee: AB-KWEKERSRECHTEN BV, Zuidwolde (NL)

( * ) Notice: Subject to any disclaimer, the term of this patent is extended or adjusted under 35 U.S.C. 154(b) by 0 days.

(21) Appl. No.: 17/185,928

(22) Filed: Feb. 25, 2021

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./428
CPC ... A01H 5/02; A01H 5/00; A01H 6/14; A01H 6/1448
See application file for complete search history.

*Primary Examiner* — June Hwu
(74) *Attorney, Agent, or Firm* — Penny J. Aguirre

(57) ABSTRACT

A new cultivar of *Echinacea* plant named 'PIN449' that is characterized by its inflorescences with ray florets that are light red-purple in color, its strong stems that do not lodge, and its compact, short plant habit.

2 Drawing Sheets

Botanical classification: *Echinacea* hybrid.
Variety denomination: 'PIN449'.

CROSS REFERENCE TO A RELATED APPLICATION

This application claims priority to European Community Plant Variety Office (CPVO) Plant Breeder's Rights Application No. 2020/2514 filed on Oct. 13, 2020, under 35 U.S.C. 119(f), the entire contents of which is incorporated by reference herein.

BACKGROUND OF THE INVENTION

The present invention relates to a new and distinct cultivar of *Echinacea* of hybrid origin and will be referred to hereafter by its cultivar name, 'PIN449'. 'PIN449' represents a new cultivar of coneflower, an herbaceous perennial grown for landscape use.

The new cultivar arose from an ongoing breeding program by the Inventor in Zuidwolde, The Netherlands with the objective of selecting new cultivars of *Echinacea* with strong plant habits and unique inflorescence colors. The new cultivar was selected as a unique seedling in a trial field by the Inventor in Zuidwolde, The Netherlands in July of 2018. The parentage of 'PIN449' is therefore unknown.

Asexual propagation of the new cultivar was first accomplished by tissue culture using meristematic tissue in Heerhugowaard, The Netherlands in January of 2019 under the direction of the Inventor. Asexual propagation by tissue culture has determined that the characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'PIN449' as a unique cultivar of *Echinacea*.

1. 'PIN449' exhibits inflorescences with ray florets that are light red-purple in color.
2. 'PIN449' exhibits strong stems that do not lodge.
3. 'PIN449' exhibits a compact, short plant habit.

The new cultivar can be most closely compared to the cultivars 'Ech391' (U.S. Plant Pat. No. 30,410) and 'Hope' (U.S. Plant Pat. No. 17,194). 'Ech391' and 'Hope' are both similar to 'PIN449' in inflorescence shape. 'Ech391' differs from 'PIN449' in having a slightly lower plant height, inflorescences that are larger in diameter, and ray florets that are yellow in color with bases that are red-purple in color. 'Hope' differs from 'PIN449' in having a taller plant height, inflorescences that are larger in diameter, and ray florets that are lighter red-purple in color with bases that are lighter red-purple in color.

BRIEF DESCRIPTION OF THE DRAWINGS

The plants in the accompanying photographs depict the characteristics of two-year-old plant of 'PIN449' as grown in a 19-cm container in Zuidwolde, The Netherlands.

The photograph in FIG. 1 provides a side view of 'PIN449' in bloom.

Figure 1:
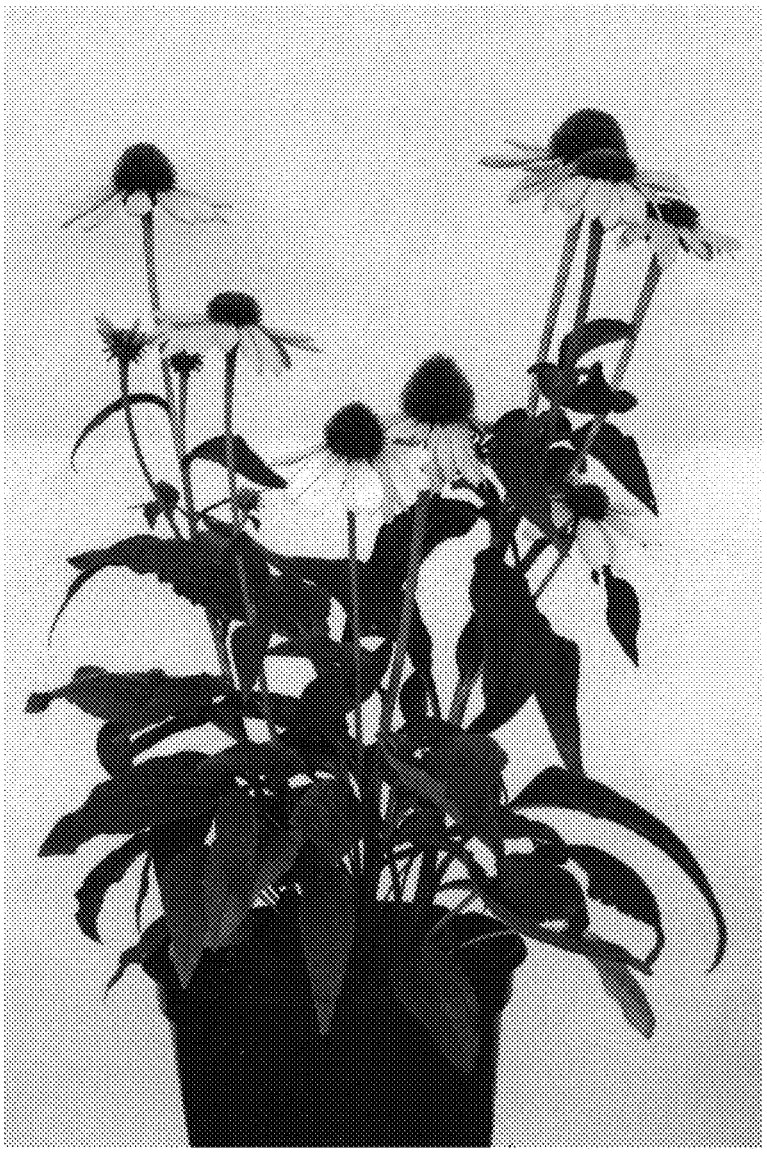
Figure 2:
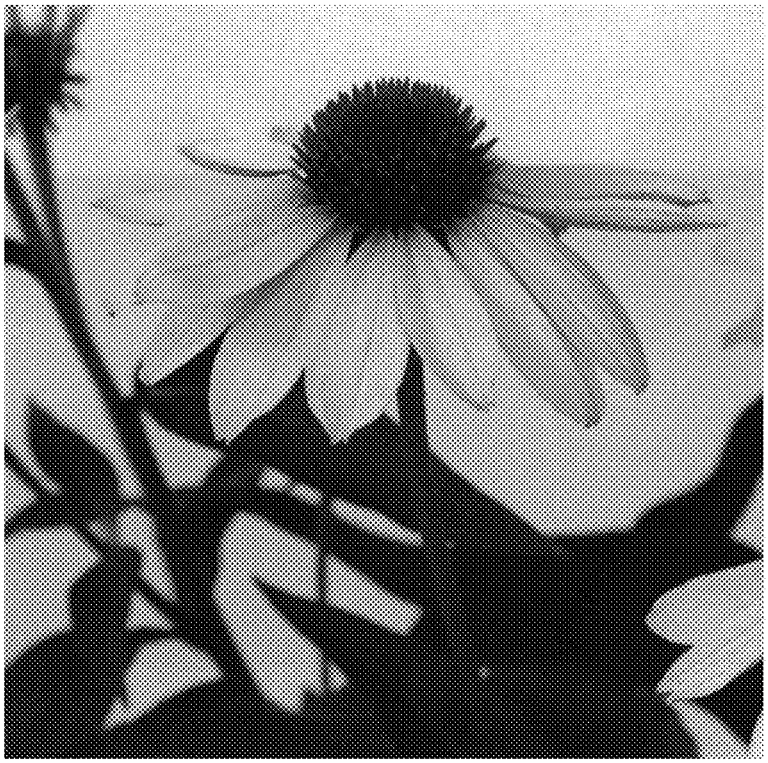

The photograph in FIG. 2 provides a close-up view of an inflorescence of 'PIN449'.

Figure 3:
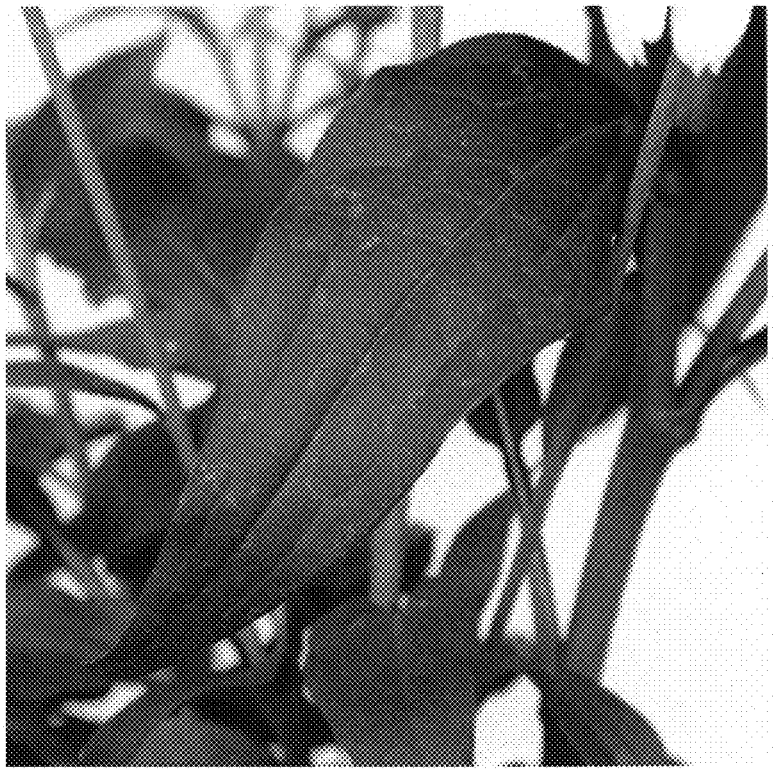

The photograph in FIG. 3 provides a close-up view of the foliage of 'PIN449'.

The colors in the photograph may differ slightly from the color values cited in the detailed botanical description, which accurately describe the colors of the new *Echinacea*.

BOTANICAL DESCRIPTION OF THE PLANT

The plants in the accompanying photographs depict the characteristics of two-year-old plants of 'PIN449' as grown in 19-cm containers in Zuidwolde, The Netherlands. The phenotype of the new cultivar may vary with variations in environmental, climatic, and cultural conditions, as it has not been tested under all possible environmental conditions.

The color determination is in accordance with The 2015 Colour Chart of The Royal Horticultural Society, London, England, except where general color terms of ordinary dictionary significance are used.

General description:

*Blooming period.*—Approximately 10 weeks from summer and late summer (July until late September) in The Netherlands.

*Plant type.*—Herbaceous perennial.

*Plant shape.*—Oblong to ovate.

*Plant habit.*—Compact, upright, short.

*Height and spread.*—Average of 47.6 cm in height, 37.3 cm in width.

*Hardiness.*—At least in U.S.D.A. Zones 4 to 9.

*Diseases and pests.*—No resistance or susceptibility to pests or diseases has been observed.

*Root description.*—Fibrous.

*Propagation.*—Tissue culture.

*Root development.*—An average of 10 weeks for root development with a finished plant produced in about 3 months.

*Growth rate.*—Moderate.

Stem description:

*Shape.*—Rounded.

*Stem color.*—144B and 146D, 144A.

*Stem size.*—Average of 5 mm in diameter and an average of 15.3 cm in length.

*Stem surface.*—Rough to the touch, moderately covered with short strigose hairs; 0.4 mm in length, N155A in color.

*Stem strength.*—Very strong.

*Stem aspect.*—Stems grow in an average angle of 15° from the base (0°=vertical).

*Branching.*—Main flowering stems grow from the base with a few lateral branches present, average of 4 primary branches, 2 branches per primary stem.

Foliage description:

*Leaf shape.*—Basal leaves; ovate, cauline leaves; narrow ovate to ovate.

*Leaf division.*—Simple.

*Leaf base.*—Attenuate.

*Leaf apex.*—Narrowly acute to acute.

*Leaf venation.*—Pinnate, upper surface; 145D, lower surface; 145C.

*Leaf margins.*—Entire, moderately undulate.

*Leaf attachment.*—Petiolate.

*Leaf arrangement.*—Alternate.

*Internode length.*—An average of 2.4 cm.

*Leaf size.*—Basal leaves; 13.5 cm in length, 7.5 cm in width, cauline leaves; 12.3 cm in length, 3.9 cm in width.

*Leaf color.*—Young upper surface; 137A and 137B, young lower surface; 147B, mature upper surface; NN137A, mature lower surface; 147B.

*Leaf surface.*—Both surfaces are slightly glossy, rough to the touch and moderately covered with very short strigose hairs; average length of 0.3 mm, 156D in color.

*Petioles.*—On basal leaves an average of 15.8 cm in length and 2.5 mm in diameter, on cauline stem leaves V-shaped an average of 2.3 cm in length and 3.5 mm in diameter, surface is smooth and glabrous, color; upper surface; 145A, very slightly to moderately tinged 182C on the margins, 187C at the base, lower surface; 145A, base 186C.

Inflorescence description:

*Type.*—Terminal capitulum, heterogamous with ray florets around the head margin and daisy-type disc florets in the center.

*Capitulum number.*—One terminal capitulum per lateral branch.

*Lastingness of inflorescence.*—About four weeks.

*Capitulum size.*—Matures to about 4 cm in height and 9.8 cm in diameter, disc is an average of 4 cm in diameter.

*Fragrance.*—Faint, sweet, pleasant.

*Involucral bracts or phyllary.*—Average of 60 arranged in 3 rows, up to 1.1 cm in length and 2 mm in width, cuneate base, acute apex, narrow ovate in shape, pointed downward into an average angle of −45°, entire margins, color; upper surface NN137A, lower surface 138B, margins 137A, upper and lower surfaces smooth, matte, moderately covered with very short hairs, average length of hairs 0.3 mm, too small to measure color.

*Buds.*—Flattened globular in shape, up to 4.2 cm in diameter and 2 cm in length, color; 146B, immature ray florets 159A, 150B at the top.

*Peduncle.*—Strong, straight on top of main (flowering) stem, average of 12.5 cm in length, 4.5 mm in diameter, color; 143A and 143B, blotches of 145A, surface is moderately covered with very short hairs an average length of 0.3 mm in length, N155A in color.

*Ray florets.*—Rotate, average of 16 (varying between 11 and 20), whorled, oblanceolate in shape, average of 4.4 cm in length and 1.45 cm in width, praemorse apex, cuneate base, entire margin, held in an average angle of −10° to horizontal, upper surface matte, moderately velvety and glabrous, lower surface very slightly glossy, sparsely pubescent average of 0.3 mm in length and too small to measure color, color; upper surface when opening 65B, base N66D, lower surface when opening 36A, tinged with 68C, tip 150B, upper surface when fully open 68D and 70D, base 60C, lower surface when fully open 36A, tinged 68C, tips 150B, upper surface fading to 158A, base N170D, lower surface fading to 160D, veined 145A and 145B.

*Disc florets.*—Numerous, average of 200, tubular, lower 80% fused, base fused into tube, arranged spirally on disc, average of 1 cm in length and 3 mm in width, entire margin, both surfaces glabrous, moderately glossy, color; upper surface when opening and fully open 145D, top 144A, lower surface when opening and fully open 146D, upper half slightly 146C.

*Receptacle.*—Ovate in shape, average of 1.1 cm in height and 1 cm in diameter, 157C to 157D in color.

*Receptacle spines.*—An average of 200 per disc floret, acicular in shape, acute apex, attenuate base, 1.2 cm in length, 2 mm in diameter, glabrous and glossy surface, color: apex 28A, apex mid-section 16A, mid-section 145A, base 145C.

Reproductive organs (present on disc florets only):

*Gynoecium.*—Pistil; 1, 7 mm in length, stigma; unequal, decurrent, 4 mm in length, 152B, style; 5.5 mm in length and 145C in color, ovary; 157D in color.

*Androecium.*—Stamens; 5, filaments; 3.5 mm in length, 154C in color, anther; linear in shape, 3.5 mm in length and 200A in color, pollen; moderate, 17B in color.

*Fruit/seed.*—No fruit or seed detected to date.

It is claimed:

1. A new and distinct cultivar of *Echinacea* plant named 'PIN449' substantially as herein illustrated and described.

* * * * *